United States Patent [19]

Zilch et al.

[11] Patent Number: 5,397,794
[45] Date of Patent: Mar. 14, 1995

[54] USE OF THIAZOLOISOINDOLINONE DERIVATIVES AS ANTIVIRAL MEDICAMENTS

[75] Inventors: Harald Zilch, Mannheim; Alfred Mertens, Schriesheim; Herbert Leinert, Heppenheim; Ulrike Leser, Munich; Bernhard König, Berg; Hans Seidel, Tutzing, all of Germany

[73] Assignee: Boehringer Mannheim GmbH, Germany

[21] Appl. No.: 50,067

[22] PCT Filed: Nov. 6, 1991

[86] PCT No.: PCT/EP91/02101

§ 371 Date: Jul. 20, 1993

§ 102(e) Date: Jul. 20, 1993

[87] PCT Pub. No.: WO92/08457

PCT Pub. Date: May 29, 1992

[30] Foreign Application Priority Data

Nov. 10, 1990 [DE] Germany .................. 40 35 809.7

[51] Int. Cl.[6] ............................................. A61K 31/425
[52] U.S. Cl. ..................................... 514/366; 514/934
[58] Field of Search ............................ 514/366, 934

[56] References Cited

PUBLICATIONS

Yaechoan et al, 1989, Pharm Ther. vol. 40 pp. 329–348.

Primary Examiner—Raymond J. Henley, III
Assistant Examiner—Russell Travers
Attorney, Agent, or Firm—Nikaido, Marmelstein, Murray & Oram

[57] ABSTRACT

The present invention concerns the use of compounds of the general formula I

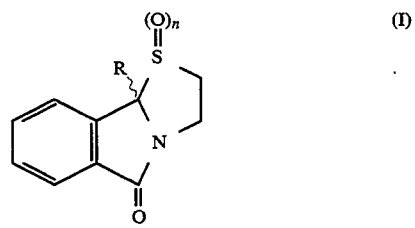

for the preparation of medicaments for the treatment of viral or retroviral infections, whereby R signifies a hydrogen atom or a straight-chained or branched, saturated or unsaturated alkyl radical with 1–7 carbon atoms, which can possibly be substituted by phenyl, or a phenyl ring which can possibly be substituted one or more times by $C_1$–$C_4$-alkyl, $C_1$–$C_4$-alkoxy, hydroxyl, trifluoromethyl, methylsulphonyl or halogen, such as fluorine, chlorine or bromine, n stands for the numbers 0, 1 or 2, as well as of their pharmacologically compatible salts or tautomers.

5 Claims, No Drawings

USE OF THIAZOLOISOINDOLINONE DERIVATIVES AS ANTIVIRAL MEDICAMENTS

The subject of the present invention is the new use of thiazoloisoindolinone derivatives for the preparation of medicaments with antiviral action.

The present invention concerns the use of compounds of the general formula I

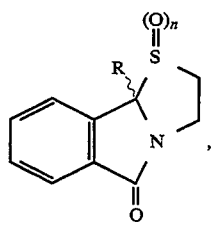

for the preparation of medicaments for the treatment of viral or retroviral infections, whereby R signifies a hydrogen atom or a straight-chained or branched, saturated or unsaturated aliphatic radical with 1–7 carbon atoms, which can possibly be substituted by phenyl, or a phenyl ring, which can possibly be substituted one or more times by $C_1$–$C_4$-alkyl, $C_1$–$C_4$-alkoxy, hydroxyl, trifluoromethyl, $C_1$–$C_4$-alkylsulphonyl or halogen, such as fluorine, chlorine or bromine, n stands for the numbers 0, 1 or 2, as well as of their pharmacologically compatible salts and tautomers.

In U.S. Pat. No. 3,334,113 is described, inter alia, 9b-phenyl-2,3-dihydrothiazolo[2,3-a]isoindol-5(9bH)-one as inflammation-inhibiting and anti-convulsive medicament. Further derivatives of thiazoloisoindolinone with similar action and lower toxicity are known from the Swiss Patent Application CH-469,733 (R=alkyl, n=0) and the Belgian Patent Application 659,528 or the U.S. Pat. No. 3,646,022, respectively.

In U.S. Pat. No. 2,860,985 and Belgian Patent Application 564,592, thiazoloisoindolinones are used for the stabilisation and as contrast agents for photographic emulsions.

Apart from in the above-mentioned Patent Applications, the synthesis of the compounds is also described in J. Org. Chem., 30, 1506 (1965), as well as in J. Org. Chem., 34, 165 (1969).

Surprisingly, it has now been found that these compounds display an outstanding anti-viral action and are, therefore, especially well suited for the treatment of viral and retroviral infections. Viral infections of mammals, especially of humans, are very widespread. In spite of intensive efforts, hitherto it has not been possible to make available chemotherapeutic agents which interfere causatively or symptomatically with occurrences of diseases caused virally or retrovirally with recognisable substantial success. At present, it is not possible to cure or chemotherapeutically favourably to influence the symptoms of certain viral diseases, such as for example acquired immune deficiency syndrome (AIDS), the AIDs-related complex (ARC) and its preliminary stages, herpes, cytomegalovirus (CMV), influenza and other viral infections. At present, for example, for the treatment of AIDS, there is almost exclusively available 3′-azido-3′-desoxythymidine (AZT), known as zidovudine or Retrovir ®. However, AZT is characterised by a very narrow therapeutic range and by very severe toxicities already arising in the therapeutic range (Hirsch, M. S. (1988), J. Infec. Dis. 157, 427–431). The compounds of the general formula I do not possess these disadvantages. They act anti-virally without being cytotoxic in pharmacologically relevant doses.

The compounds of the present invention display valuable pharmacological properties. In particular, they are suitable for the therapy and prophylaxis of infections which are caused by DNA viruses, such as e.g. the herpes simplex virus, the cytomegalovirus, papillomaviruses, varicalla zoster virus or Epstein-Barr virus, or RNA viruses, for example toga-viruses, or especially retroviruses, such as onco-viruses HTLV-I and II, as well as the lentiviruses visna and the human immune deficiency virus HIV-1 and 2.

The compounds of the formula I appear to be especially suitable for the treatment of the clinical manifestations of the retroviral HIV infection in humans, such as the persistent, generalised lymphadenopathy (PGL), the advance stage of the AIDS-related complex (ARC) and the clinically complete manifestation of AIDS.

It could now be demonstrated that compounds of the general formula I inhibit the multiplication of DNA and RNA viruses at the stage of the virus-specific DNA and RNA transcription, respectively. Via the inhibition of the enzyme reverse transcriptase, the substances can influence the multiplication of retroviruses (cf. Proc. Natl. Acad. Sci. USA, 83, 1911, 1986 and Nature, 325, 773, 1987).

Since a very great need exists for chemotherapeutics which interfere as specifically as possible with retrovirally-caused diseases or their symptoms without influencing the normally occurring natural body functions, the said compounds could advantageously be used prophylactically or therapeutically in the case of the treatment of diseases in which a retroviral infection is of pathophysiological, symptomatic or clinical relevance.

In the formula I, R signifies a straight-chained or branched, saturated or unsaturated aliphatic radical, especially an alkyl radical with 1–7, preferably 1–4 carbon atoms, such as e.g. methyl, ethyl or isopropyl. The aliphatic radical can also be substituted by a phenyl group so that R represents a phenylalkyl radical, such as e.g. benzyl. As unsaturated radicals, there come into question $C_2$–$C_7$-alkenyl or $C_2$–$C_7$-alkynyl groups. Furthermore, R can represent a phenyl ring which can be unsubstituted or substituted one or more times. The phenyl ring is preferably substituted once or twice. As substituents, there come into question, for example, the methyl, ethyl, methoxy or ethoxy group.

R preferably signifies a phenyl group which can be substituted one to three times by the following radicals: $C_1$–$C_4$-alkyl, especially methyl, ethyl, n-propyl or i-propyl; halogen, especially fluorine, chlorine or bromine; trifluoromethyl, hydroxyl, $C_1$–$C_4$-alkoxy, especially methoxy or ethoxy. Especially preferred are those derivatives which carry a substituent in the 3- or 4-position of the phenyl ring. Disubstituted phenyl raducals are preferably the derivatives substituted in the 3,5-, 3,4-, 2,4-or 2,5-position.

The medicaments containing at least one compound of the formula I can be administered enterally or parenterally in liquid or solid form for the treatment of viral infections. There hereby come into question the usual forms of administration, such as for example tablets, capsules, coated tablets, syrups, solutions or suspensions. As injection medium, water is preferably used which contains the additives usual in the case of injection solutions, such as stabilising agents, solubilising agents and buffers. Such additives are e.g. tartrate and citrate buffers, ethanol, complex formers, such as ethylenediamine-tetraacetic acid and its non-toxic salts, high molecular polymers, such as liquid polyethylene oxide, for viscosity regulation. Liquid carrier materials for injection solutions must be sterile and are preferably filled into ampoules. Solid carrier materials are, for example, starch, lactose, mannitol, methyl cellulose, talc, highly dispersed silicic acids, high molecular fatty acids, such as stearic acid, gelatine, agar-agar, calcium phosphate, magnesium stearate, animal and vegetable fats, solid high molecular polymers, such as polyethylene glycols, etc. Compositions suitable for oral administration can, if desired, contain flavouring and sweetening agents.

The dosage can depend upon various factors, such as mode of administration, species, age or individual state of health. The compounds according to the invention are usually administered in amounts of 0.1–100 mg, preferably 0.2–80 mg per day and per kg of body weight. It is preferred to divide up the daily dose into 2–5 administrations, whereby, in the case of each administration, 1–2 tablets are given with an active material content of 0.5–500 mg. The tablets can also be retarded, whereby the number of administrations per day are reduced to 1–3. The active material content of the retarded tablets can amount to 2–1000 mg. The active material can also be given by continuous infusion, whereby the amounts of 5–1000 mg per day normally suffice.

The compounds according to the invention of the general formula I can be prepared according to procedures of the patent specifications and literature references mentioned in the prior art.

Apart from the compounds mentioned in the Examples and those obtained by the combination of all of the meanings given in the claims for the substituents, in the meaning of the present invention, the following compounds of the formula I come into question:
1. 9b-(2,4-dimethylphenyl)-2,3-dihydrothiazolo-[2,3-a]-isoindol-5(9bH)-one
2. 9b-(4-trifluoromethylphenyl)-2,3-dihydrothiazolo-[2,3-a]isoindol-5(9bH)-one
3. 9b-(4-ethoxyphenyl)-2,3-dihydrothiazolo-[2,3-a]-isoindol-5(9bH)-one
4. 9b-(3-fluorophenyl)-2,3-dihydrothiazolo[2,3-a]-isoindol-5(9bH)-one
5. 9b-(4-methylsulphonylphenyl)-2,3-dihydrothiazolo-[2,3-a]-isoindol-5(9bH)-one
6. 9b-phenyl-2,3-dihydrothiazolo[2,3-a]isoindol-5(9bH)-one 1-oxide.

EXAMPLE 1

Inhibition of reverse transcriptase (RT) by 9b-phenyl-2,3-dihydrothiazolo[2,3-a]isoindol-5(9bH)-one.

The screening test system contains the purified RT from HIV-1, which was expressed by gene-technological methods in E. coli, as well as the components of the initiation complex, such as the in vitro transcripts of the HIV-LTR's with the neighbouring primer binding site as template and an 18 mer oligo-nucleotide as primer complementary to the primer binding site. The [$-^3$H]-thymidine-5'-triphosphate incorporation was measured by counting in a $\beta$-counter. Results:

| substance | inhibition of the HIV-RT $IC_{50}$ [M] |
| --- | --- |
| 3'-azido-3'-desoxy-thymidine-5'-triphosphate [AZT-TP] | $6.0 \times 10^{-6}$ |
| 3.2 | $4.0 \times 10^{-6}$ |
| 3.4 | $4.0 \times 10^{-6}$ |
| 3.8 | $0.8 \times 10^{-6}$ |
| 3.12 | $1.1 \times 10^{-6}$ |
| 3.15 | $1.0 \times 10^{-6}$ |
| 3.18 | $0.95 \times 10^{-6}$ |
| 3.30 | $0.7 \times 10^{-6}$ |
| 4 | $1.4 \times 10^{-6}$ |

EXAMPLE 2

2,3-Dihydrothiazolo[2,3-a]isoindol-5(9bH)-one was prepared in a yield of 64% analogously to J. Am. Chem. Soc. 80, 702 (1958) and recrystallised from ethanol.

M.P. 101°–102° C. (lit. 97°–100° C.).

EXAMPLE 3

9b-(3,5-dimethylphenyl)2,3-dihydrothiazolo[2,3-a]-isoindol-5(9bH)-one 10 mmol 2-(3,5-dimethylbenzoyl)-benzoic acid were dissolved in 100 ml of xylene and, after addition of 20 mmol cysteamine, as well as a catalytic amount of p-toluenesulphonic acid, heated for 2 h under reflux on a water separator. The solvent was then removed in a vacuum and the residue recrystallised from ethanol. Yield 53%, m.p. 163° C.

The following compounds were prepared analogously to Example 3:

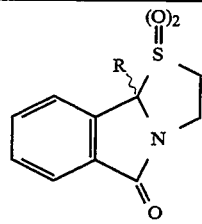

| example | R | yield | m.p. °C. |
| --- | --- | --- | --- |
| 3.1 | 4-methoxyphenyl | 31% | oil |
| 3.2 | 4-chlorophenyl | 47% | 127–131 |
| 3.3 | 4-methylphenyl | 81% | 72–75 |
| 3.4 | 3,4-dichlorophenyl | 60% | oil |
| 3.5 | 3,4-dimethylphenyl | 51% | 155–157 |
| 3.6 | 4-isopropylphenyl | 30% | oil |
| 3.7 | 3-methylphenyl | 78% | 120–122 |
| 3.8 | 2,3-dimethylphenyl | 74% | 191–195 |
| 3.9 | 3-isopropylphenyl | 42% | 99–101 |
| 3.10 | 3-ethylphenyl | 27% | oil |
| 3.11 | 3-chlorophenyl | 49% | 132–134 |
| 3.12 | 3-methoxyphenyl | 49% | 141 |
| 3.13 | 3,5-dichlorophenyl | 77% | 108 |
| 3.14 | 4-fluorophenyl | 56% | 68 |
| 3.15 | 3-trifluoromethylphenyl | 40% | 105 |
| 3.16 | 2-hydroxy-4-methoxyphenyl | 37% | 176 |
| 3.17 | 4-hydroxyphenyl | 43% | 240 |
| 3.18 | 2,5-dimethylphenyl | 74% | 91 |
| 3.19 | 4-bromophenyl | 66% | 145–147 |
| 3.20 | 3-hydroxyphenyl | 45% | 138–140 |
| 3.21 | 4-ethylphenyl | 71% | oil |
| 3.22 | 2-chlorophenyl | 49% | 150 |
| 3.23 | 2-methylphenyl | 37% | 110 |
| 3.24 | benzyl | 18% | 106–110 |
| 3.25 | pentyl | 72% | oil |
| 3.26 | butyl | 61% | oil |

-continued (structure with (O)₂=S, R, phenyl fused ring, N, C=O)

| example | R | yield | m.p. °C. |
|---|---|---|---|
| 3.27 | methyl | 48% | oil |
| 3.28 | propyl | 77% | 78–83 |
| 3.29 | hexyl | 67% | oil |
| 3.30 | phenyl | 91% | 108–110 |

EXAMPLE 4

9b-Phenyl-2,3-dihydrothiazolo[2,3-a]isoindol-5(9bH)-one 1,1-dioxide 1.3 g 9b-phenyl-2,3-dihydrothiazoloe[2,3-a]isoindol-5(9bH)-one were dissolved in 12.5 ml dichloromethane and mixed with a solution of 1.54 g $KMnO_4$ in 25 ml $H_2O$, as well as 0.6 g of benzyltriethylammonium chloride. After stirring for 4 h at RT, the organic phase was separated off, washed twice with $H_2O$, and, after drying over $Na_2SO_4$, evaporated. The residue was purified by column chromatography on silica gel 60 with dichloromethane/methanol 9/1 as eluent and crystallised from ether. Yield 0.77 g (53% of theory); m.p. 190°–193° C.

EXAMPLE 5

9b-Phenyl-2,3-dihydrothiazolo[2,3-a]isoindol-5(9bH)-one 1-oxide 0.5 g 9b-phenyl-2,3-dihydrothiazolo[2,3-a]-isoindol-5(9bH)-one were dissolved in 5 ml glacial acetic acid and, after addition of 0.2 ml 30 percent $H_2O_2$, stirred for 10 h at RT. After half of the time, a further 0.2 ml 30 percent $H_2O_2$ were added thereto.

After the given time, the batch was evaporated and the residue purified by column chromatography on silica gel 60 with dichloromethane/methanol 97/3 as eluent. Yield 145 mg (27% of theory); m.p. 174°–177° C.

We claim:

1. A method of treating a patient suffering from a retroviral infection comprising administering to said patient a therapeutically effective amount of a compound of Formula I

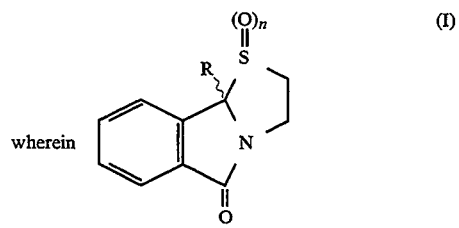

wherein

R is selected from the group consisting of hydrogen; $C_1$–$C_7$ alkyl, $C_2$–$C_7$ alkene, $C_2$–$C_7$ alkyne, wherein the alkyl, alkene, or alkyne is unsubstituted or substituted with phenyl; and a phenyl ring which is unsubstituted or substituted at least once with $C_1$–$C_4$ alkyl, $C_1$–$C_4$ alkoxy, hydroxyl, trifluoromethyl, $C_1$–$C_4$ is 0, 1, or 2; or a salt a tautomer thereof.

2. The method of claim 1 wherein R is hydrogen, $C_1$–$C_7$ alkyl, $C_2$–$C_7$ alkene, or $C_2$–$C_7$ alkyne, wherein the alkyl, alkene, or alkyne is unsubstituted or substituted with phenyl.

3. The method of claim 1 wherein R is $C_1$–$C_7$ alkyl, $C_2$–$C_7$ alkene, or $C_2$–$C_7$ alkyne, wherein the alkyl, alkene, or alkyne is unsubstituted or substituted with phenyl.

4. The method of claim 1 wherein R is a phenyl ring which is unsubstituted or substituted one to three times with $C_1$–$C_4$ alkyl, $C_1$–$C_4$ alkoxy, hydroxyl, or halogen.

5. The method of claim 1 wherein the compound is selected from the group consisting of:
9b-phenyl-2,3-dihydrothiazolo[2,3-a]isoindol-5(9bH)-one
9b-(4-methylphenyl)-2,3-dihydrothiazolo[2,3-a]isoindol-5(9bh)-one
9b-(3,4-dimethylphenyl)-2,3-dihydrothiazolo[2,3-a]isoindol-5(9bH)-one
9b-(3-methylphenyl-2,3-dihydrothiazolo[2,3-a]isoindol-5(9bH)-one
9b-(3-chlorophenyl)-2,3-dihydrothiazolo[2,3-a]isoindol-5(9bH)-one
9b-(3,5-dichlorophenyl)-2,3-dihydrothiazolo[2,3-a]isoindol-5(9bH)-one
9b-(4-chlorophenyl)-2,3-dihydrothiazolo[2,3-1]isoindol-5(9bH)-one
9b-(3-methylphenyl)-2,3-dihydrothiazolo[2,3-a]isoindol-5(9bH)-one.

* * * * *